US008606345B2

(12) United States Patent
Taylor et al.

(10) Patent No.: US 8,606,345 B2
(45) Date of Patent: Dec. 10, 2013

(54) MEDICAL DUAL LENS CAMERA FOR DOCUMENTATION OF DERMATOLOGICAL CONDITIONS WITH LASER DISTANCE MEASURING

(75) Inventors: John David Taylor, Pittsburg, KS (US); Gregory Allen Yotz, Gridley, KS (US); Michael Dave Shaw, Baxter Springs, KS (US); Robert Samuel Burkhalter, Jasper, MO (US); James Michael Burgess, Pittsburg, KS (US); Richard Kent Richardson, Baxter Springs, KS (US)

(73) Assignee: GSM OF KANSAS, Inc., Pittsburg, KS (US)

( * ) Notice: Subject to any disclaimer, the term of this patent is extended or adjusted under 35 U.S.C. 154(b) by 294 days.

(21) Appl. No.: 12/872,357

(22) Filed: Aug. 31, 2010

(65) Prior Publication Data

US 2011/0054310 A1   Mar. 3, 2011

Related U.S. Application Data

(60) Provisional application No. 61/275,470, filed on Aug. 31, 2009.

(51) Int. Cl.
*A61B 5/05* (2006.01)
(52) U.S. Cl.
USPC ............................ 600/407; 600/427; 600/160
(58) Field of Classification Search
USPC ................ 600/160, 167, 427; 356/5.05, 4.05; 348/348
See application file for complete search history.

(56) References Cited

U.S. PATENT DOCUMENTS

| 2,437,916 A | 3/1948 | Greenwald |
| 4,170,987 A | 10/1979 | Anselmo et al. |
| 4,693,255 A | 9/1987 | Beall |

(Continued)

OTHER PUBLICATIONS

Fuji Fine Pix 3D, 2008.*

(Continued)

*Primary Examiner* — Unsu Jung
*Assistant Examiner* — Serkan Akar
(74) *Attorney, Agent, or Firm* — Mark D. Bowen; Malin Haley DiMaggio & Bowen, P.A.

(57) ABSTRACT

An imaging apparatus in accordance with the present invention comprises a hand-held, battery powered imaging device that provides: (1) an Identification Picture wherein an image of the patient's face is captured for identification purposes; (2) an Area of Interest picture wherein an image of the general area of interest on the patient is captured; and (3) a Subject of Interest picture wherein an image of the subject lesion of interest is captured. Two digital imaging systems, including a wide-angle (e.g. fisheye) imaging system and a macro (close-up) imaging system, are provided to allow for the simultaneous capture of AOI and SOI images thereby capturing an image that identifies the location of the lesion on the body and an image that comprises a close-up view of the lesion. A light source or flash provides illumination during the image capture phase. A laser range finding configuration including spaced first and second lasers are angularly disposed so as to cast beams that intersect at a desired distance from the imaging apparatus thereby allowing the user to quickly position the imaging apparatus at a predetermined distance from the patient when capturing images. Audible output provides the user with input to assist in properly capturing the images, and a trigger-type actuator is provided to initiate image capture.

4 Claims, 5 Drawing Sheets

(56) References Cited

U.S. PATENT DOCUMENTS

| | | |
|---|---|---|
| 4,905,702 A | 3/1990 | Foss |
| 5,146,923 A | 9/1992 | Dhawan |
| 5,836,877 A | 11/1998 | Zavislan |
| 6,032,071 A | 2/2000 | Binder |
| 6,208,749 B1 | 3/2001 | Gutkowicz-Krusin et al. |
| 6,215,893 B1 | 4/2001 | Leshem et al. |
| 6,277,067 B1 * | 8/2001 | Blair ............................ 600/167 |
| 6,427,022 B1 | 7/2002 | Craine et al. |
| 6,603,552 B1 | 8/2003 | Cline et al. |
| 6,684,092 B2 | 1/2004 | Zavislan |
| 7,162,063 B1 | 1/2007 | Craine et al. |
| 7,298,881 B2 | 11/2007 | Giger et al. |
| 7,522,825 B2 | 4/2009 | Kenet |
| 7,657,101 B2 | 2/2010 | Christiansen, II et al. |
| 2002/0176020 A1 * | 11/2002 | Kawaguchi et al. .......... 348/373 |
| 2005/0041143 A1 * | 2/2005 | Kakiuchi et al. ............... 348/370 |
| 2005/0214444 A1 * | 9/2005 | Robens et al. .................... 427/8 |
| 2006/0092315 A1 | 5/2006 | Payonk et al. |
| 2008/0164316 A1 * | 7/2008 | Patel et al. ............... 235/462.43 |

OTHER PUBLICATIONS

Plassmann et al. Good Practice Guide to the use of MAVIS II, Jul. 2006.*

* cited by examiner

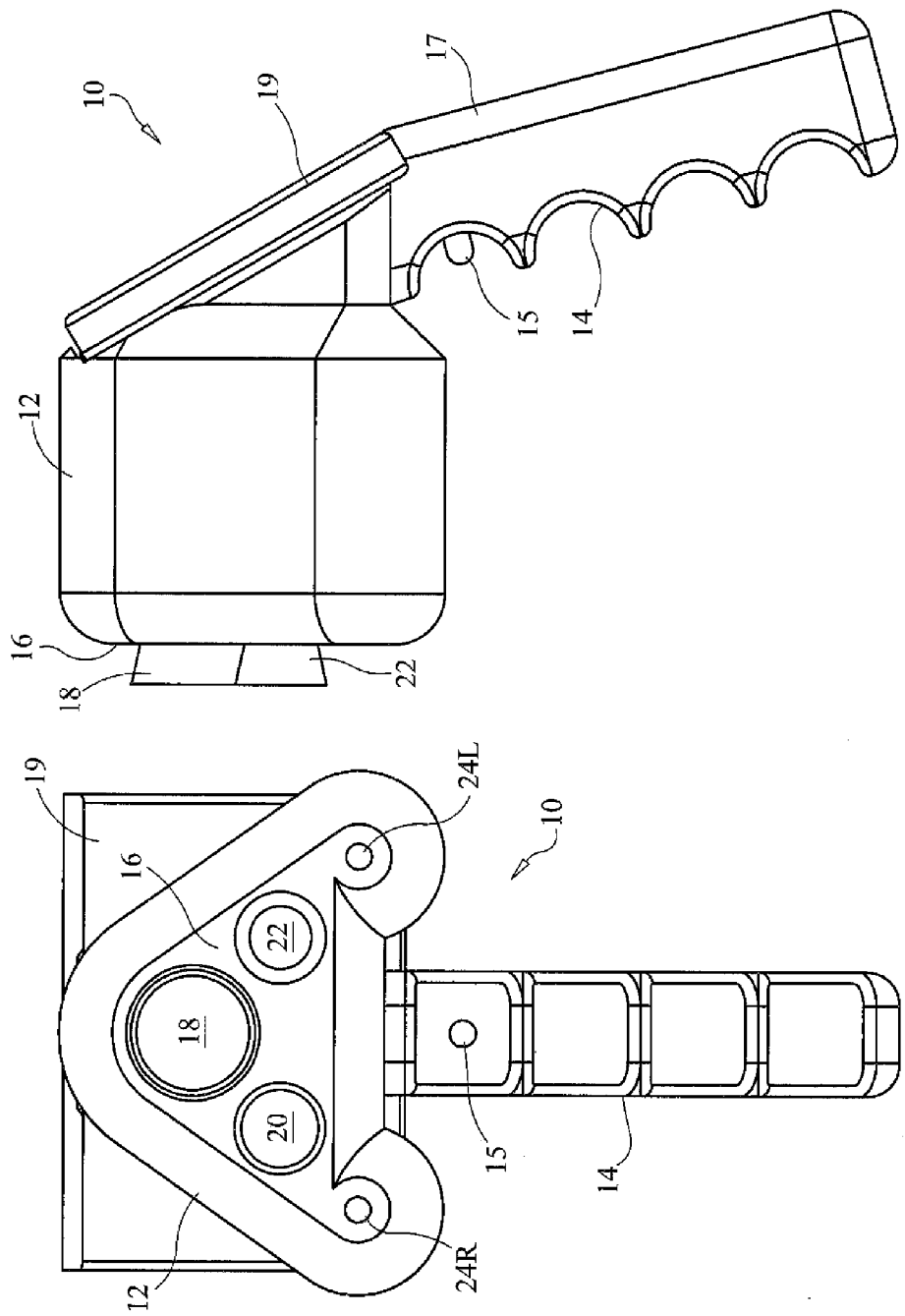

MEDICAL DUAL LENS CAMERA FOR DOCUMENTATION OF DERMATOLOGICAL CONDITIONS WITH LASER DISTANCE MEASURING

CROSS REFERENCE TO RELATED APPLICATIONS

This application claims the benefit of provisional U.S. Patent Application Ser. No. 61/275,470, filed on Aug. 31, 2009.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

The present invention relates to apparatus and methods for use in dermatological screening, monitoring, documentation, and diagnosis of skin conditions, and more particularly to a portable hand-held medical imaging apparatus for documenting areas and subjects of interest on a patient's skin.

2. Description of Related Art

Accurately identifying skin lesions and their causes and clearly documenting this information increases diagnostic accuracy for improved treatment and healing. Such documentation should include information identifying the area of interest, and physical characteristics of the lesion, including the size, shape, configuration, color, and color of the surrounding skin. During a dermatological examination, a physician will typically conduct a visual inspection of the patient's entire body, including the scalp, hands, and feet, looking for suspicious growths, moles, or lesions. Monitoring and documentation of skin lesions, suspicious growths, and moles, is critical in diagnosis and treatment of dermatological disorders. In addition, advancements in medical records technology now present a need for an imaging system capable of capturing and downloading images, and associated data, relating to skin lesions, suspicious growths, and moles, to current Electronic Health Records (EHRs) so as to enable efficient data capture and tracking of the patient's progression and/or resolution of skin abnormalities.

One method commonly employed in the dermatology field to monitor patient lesions involves holding a measuring apparatus, such as a wound care template or ruler, against the skin and photographing the area using a conventional digital camera. Often, however, photographic images captured using this method are captured from different distances, angles, under different lighting conditions, and often times lack proper focus. In addition, the physician must rely exclusively on the wound care template or ruler to determine the size of the lesion or AOI.

As a result, the background art reveals various apparatus and methods for examining skin tissue and lesions. For example, U.S. Pat. No. 4,170,987, issued to Anselmo et al., discloses a skin diagnosis system that includes a scanning and optical arrangement wherein light is reflected from the skin to three separate light filters. U.S. Pat. No. 4,693,255, issued to Beall, discloses a system that relies on computerized analysis of a video recording of the kinetics of the change in appearance of the traumatized skin site. U.S. Pat. No. 4,905,702 issued to Foss, discloses an apparatus for imaging and measuring portions of the skin. U.S. Pat. No. 5,836,877, issued to Zavislan, discloses a system for facilitating pathological examination of a lesion in tissue using a computer system having a camera for producing a digital macroscopic picture of the lesion and an imaging apparatus coupled to the computer system. U.S. Pat. No. 6,215,893, issued to Leshem et al., discloses an apparatus and method for temporal comparison of skin surface images using a CCD camera adapted with telecentric optics that enable the capture of images with constant magnification independent of the camera-object distance. U.S. Pat. No. 6,603,552, issued to Cline el al., discloses a lightweight hand-held skin abnormality detection system that includes a fluorescent light source and a beam splitter which divides reference light and fluorescent light into separate optical channels, each of which produces a an image. U.S. Pat. No. 7,657,101, issued to Christiansen II discloses a device for acquiring first and subsequent images of a suspect area on a patient and methods for monitoring or detecting changes in the suspect area.

The disclosures of the background art, however, are burdened with overly complex systems and other limitations that have resulted in less than widespread commercial success and acceptance.

BRIEF SUMMARY OF THE INVENTION

The present invention overcomes the limitations and disadvantages present in the art by providing a portable hand-held medical imaging apparatus for documenting areas and subjects of interest on a patient's skin to allow for more accurate assessment and evaluation. An imaging apparatus in accordance with the present invention, is capable of producing accurate digital images of suitable quality for identification and tracking of any Area of Interest ("AOI") or any Subject of Interest ("SOI"), including the identification and tracking of distinguishing lesions and/or characteristics on a person, pet, or object.

An imaging apparatus in accordance with the present invention comprises a hand-held, battery powered imaging device that provides: (1) an Identification Picture wherein an image of the patient's face is captured for identification purposes; (2) an AOI picture wherein an image of the general area of interest on the patient is captured; and (3) an SOI picture wherein an image of the subject lesion of interest is captured. Two digital imaging systems, including a wide-angle (e.g. fisheye) imaging system and a macro (close-up) imaging system, are provided to allow for the simultaneous capture of AOI and SOI images thereby capturing an image that identifies the location of the lesion on the body and an image that comprises a close-up view of the lesion. A light source or flash provides illumination during the image capture phase. The imaging apparatus further includes a laser range finding configuration, wherein spaced first and second lasers are angularly disposed so as to cast beams that intersect at a desired distance from the imaging apparatus thereby allowing the user to quickly position the imaging apparatus at a predetermined (i.e. constant) distance from the patient when capturing images. Audible output provides the user with input to assist in properly capturing the images, and a trigger-type actuator is provided to initiate image capture.

The captured images are temporarily stored in internal memory provided with the imaging apparatus. A dock is provided for holding the imaging apparatus when not in use, while further functioning to re-charge the battery power source. The imaging apparatus is adapted to download captured images to an electronic health records ("EHR") system, via hard-wire or wireless communication. The present invention thus provides a system and method for quickly and easily capturing consistent images of skin lesions or other areas/subjects of interest to provide medical professionals with an accurate and clear history.

Accordingly, it is an object of the present invention to provide an apparatus and method for documenting areas and subjects of interest on a patient's skin to allow for more accurate assessment and evaluation.

Another object of the present invention is to provide a portable hand-held medical imaging apparatus for documenting areas and subjects of interest on a patient's skin to allow for more accurate assessment and evaluation.

Still another object of the present invention is to provide a medical imaging apparatus that simultaneously captures wide angle and close-up images.

Yet another object of the present invention is to provide a medical imaging apparatus adapted with a laser range finding capability to ensure that the imaging apparatus is accurately positioned for repeatedly reliable results.

Another object of the present invention is to provide such an apparatus to include a docking station that functions to charge an internally housed battery power source.

These and other objects are met by the present invention which will become more apparent from the accompanying drawing and the following detailed description of the drawings and preferred embodiments.

BRIEF DESCRIPTION OF THE SEVERAL VIEWS OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 1 is a front elevational view of an imaging apparatus in accordance with the present invention;

FIG. 2 is a side view thereof;

DETAILED DESCRIPTION OF THE INVENTION

Figure 4:
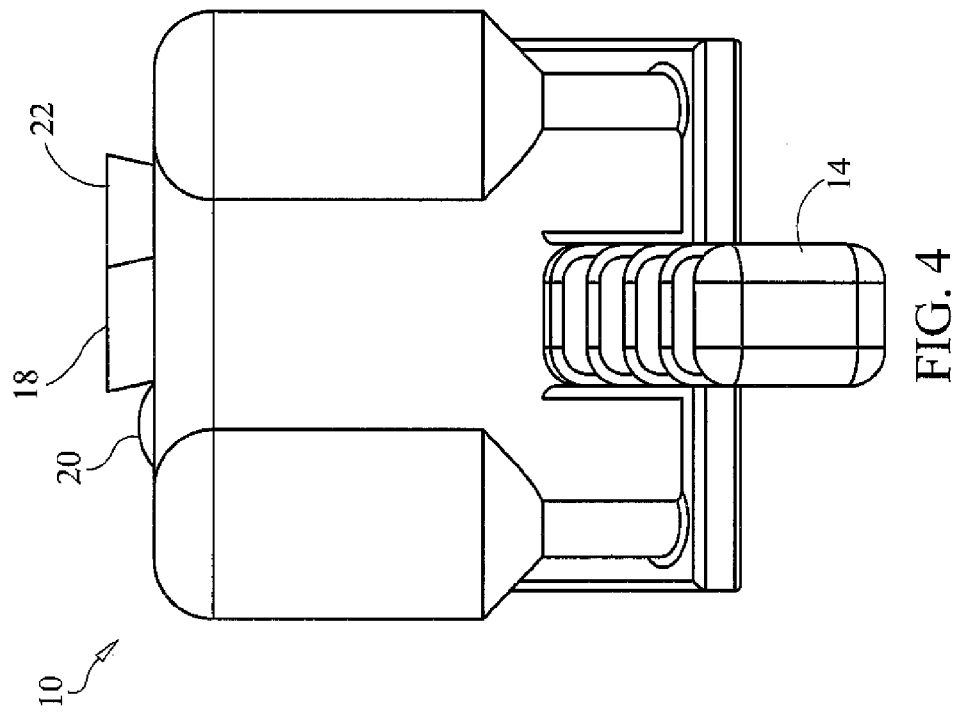
FIG. 4 is a bottom view thereof.
Figure 3:
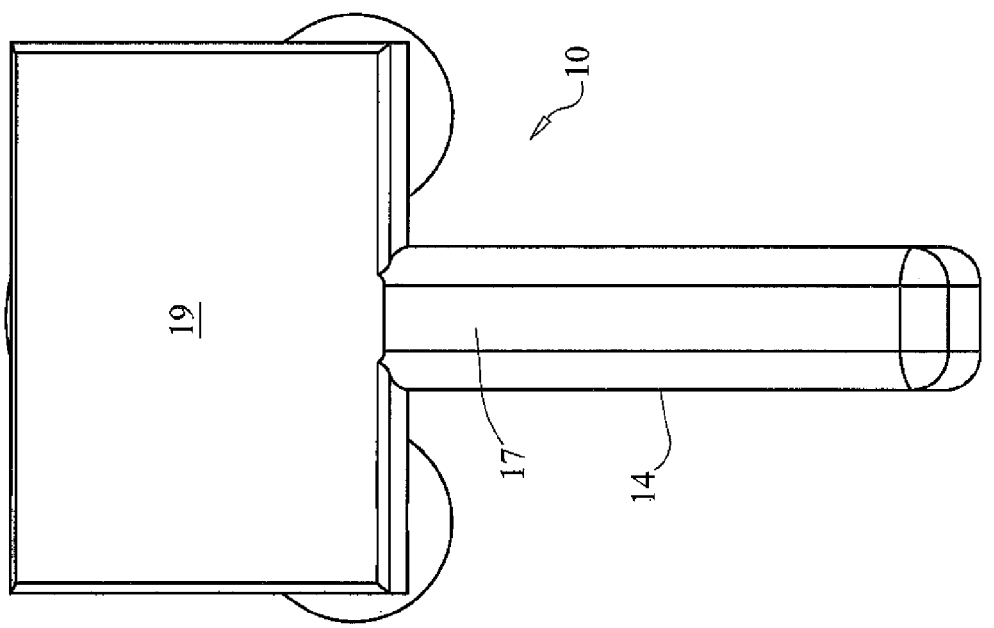
FIG. 3 is a rear view thereof.
Figure 6:
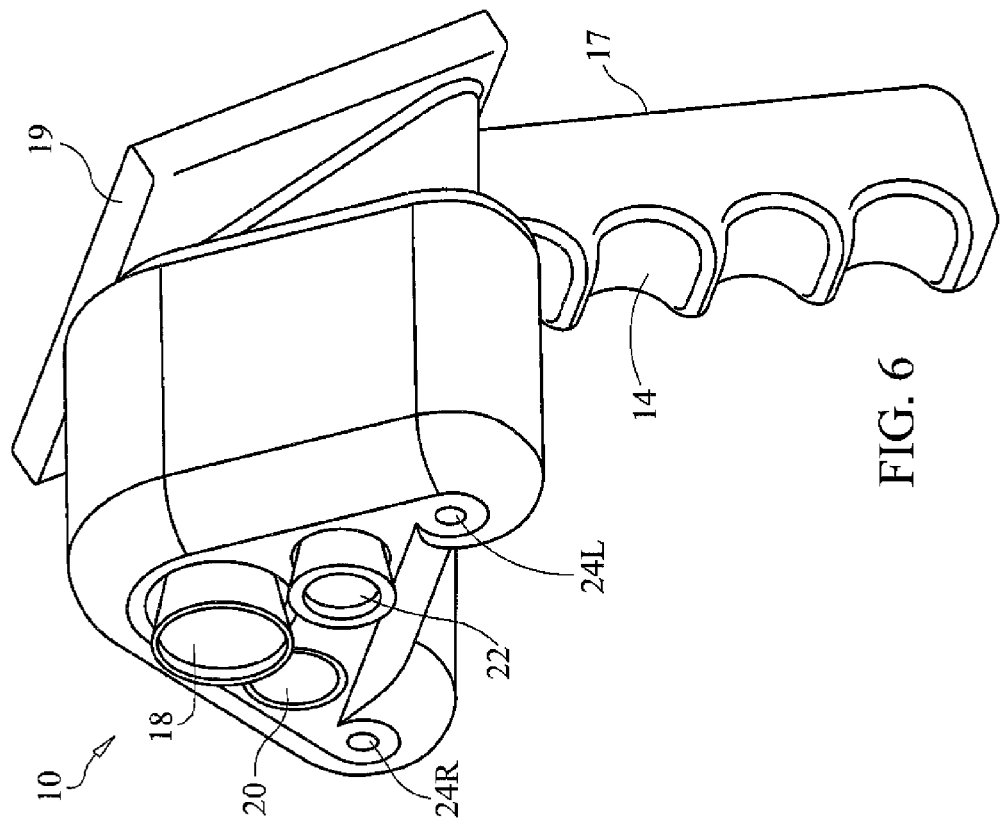
FIG. 6 is a front perspective view thereof.
Figure 5:
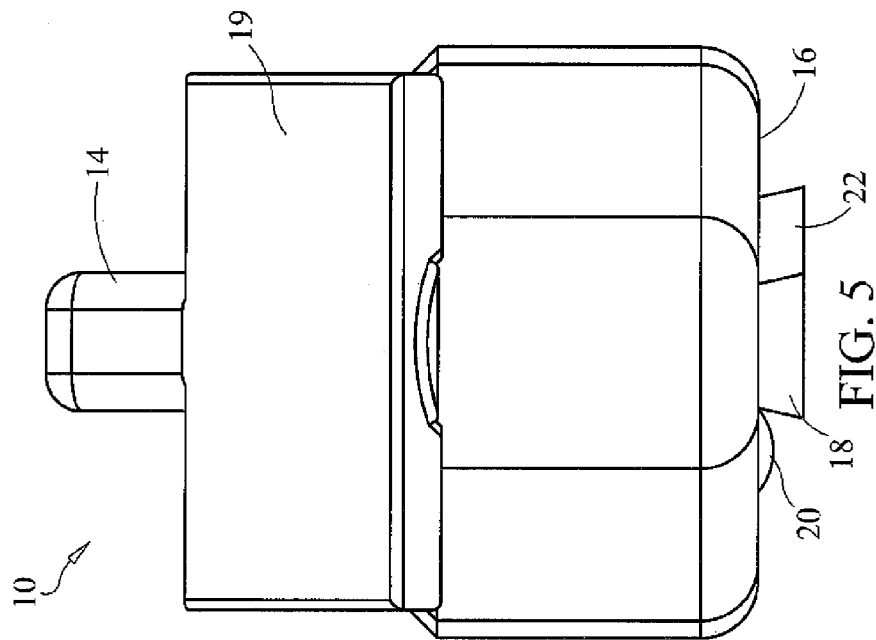
FIG. 5 is a top view thereof.

With reference now to the drawings, FIGS. 1-8 depict a preferred embodiment of a portable hand-held medical imaging apparatus, generally referenced as 10, for documenting areas and subjects of interest on a person's skin in accordance with the present invention. Imaging apparatus 10 includes a generally rigid main body or housing 12 having a grip 14 to allow a user to ergonomically grasp and manipulate imaging apparatus 10 when in use. Imaging apparatus 10 comprises a hand-held, battery powered imaging device that provides: (1) an Identification Picture wherein an image of the patient's face is captured for identification purposes; (2) an AOI picture wherein an image of the general area of interest on the patient is captured; and (3) an SOI picture wherein an image of the subject lesion of interest is captured.

Imaging apparatus 10 includes a front portion 16 adapted with a light source 18 that projects light for illumination of the patient, subject, and area of interest. Light source 18 preferably comprises a multi-wavelength light source to ensure proper illumination of the AOI and SOI such that suitable images may be obtained with proper exposure and accurate color representation. A significant aspect of the present invention involves providing an imaging apparatus 10 with two digital imaging systems with lenses disposed on the front portion 16. More particularly, imaging apparatus 10 includes a wide-angle (e.g. fisheye) imaging system 20 and a macro (close-up) imaging system 22. By providing both wide-angle and macro imaging systems, the present invention is capable of simultaneously capturing both AOI and SOI images. More particularly, the wide-angle imaging system 20 captures an Area of Interest image that comprises a view sufficient to identify exactly where on the patient's body the lesion exists. In addition, the macro imaging system 22 captures a close-up view of the lesion. By first capturing an identification image of the patient (i.e. face or ID tag) and then simultaneously capturing AOI and SOI images, the imaging apparatus of the present invention obtains a complete record that documents the patient's identity, a wide-angle view of a specific area of interest on the patient, and a close-up view of a specific subject of interest (e.g. lesion). Handle 14 is preferably adapted to include a trigger-type manual activation switch, referenced as 15, that functions to activate the apparatus. Imaging apparatus 10 further includes a back portion 17, having an electronic display 19.

A further significant aspect of the present invention involves ensuring that the imaging apparatus is accurately and repeatedly positioned a predetermined distance from the patient when capturing images. Accordingly, imaging apparatus 10 includes a pair of spaced light beam emitters, each referenced as 24 (including a left light beam emitter configuration 24L and a right light beam emitter configuration 24R), which are inwardly angled to emit beams of light to a common point spaced a predetermined distance from the front 16 of imaging apparatus 10. Light beam emitters 24 are preferably angularly adjustable to allow for calibration. Light beam emitters 24L and 24R preferably comprise low-energy laser devices so as to emit focused beams of light for maximum accuracy. In accordance with one embodiment, the user simply moves imaging apparatus 10 relative to the patient until the emitted light beams converge to form a single point or dot on the patient's skin, at which point the imaging apparatus is in properly spaced relation for image capture.

A further significant aspect of the present invention involves providing light beam emitters 24 that function to allow imaging apparatus 10 to provide the user with accurate feedback as to when imaging apparatus 10 is inside a suitable image capture window, or outside a suitable image capture window. More particularly, the laser light beam emitters 24 of the present invention are preferably modulated by the processor 32 for rapid and alternating activation and deactivation (i.e. alternating pulsed emission), such that, for example, light beam emitter 24L is activated for $1/60^{th}$ of a second while light beam emitter 24R is deactivated, followed generally immediately by the deactivation of light beam emitter 24L and concurrent activation of light beam emitter 24R for the subsequent 1/60th of a second period. Light beam emitters 24 are thus preferably subject to rapid and alternating activation/deactivation phases as the user maneuvers imaging apparatus 10 in proximity to the subject.

A further significant aspect of the present invention involves configuring imaging apparatus 10 such that processor 32 and imaging systems 20 and/or 22 track the reflectance of alternating light beam pulses so as to enable processor 32 of imaging apparatus 10 to provide a real time calculation of the distance of imaging apparatus 10 from the subject. In accordance with this aspect of the present invention, the rapidly (relative to the human eye) alternating activated beams from light beam emitters 24L and 24R are detected by the imaging systems, such that processor 32 is provided data that indicates the relative reflectance locations of beams 25L and 25R. That data allows processor 32 to determine the pixel location of beam reflectance (in generally real time) for each of the two emitted beams 25L and 25R. More particularly, the input received indicates which light beam emitter (either 24L or 24R) was activated when a reflected image was detected by one or both imaging systems 20 and/or 22, which reflected image can be identified by pixel location (e.g. pixel row and column). By comparing successive data from corresponding successive light beam emissions from both light beam emitters 24L and 24R, processor 32 is capable (via software) to determine whether the subject is within a suitable range for imaging. The present invention contemplates a range of suitable distances (e.g. between 12-inches and 18 inches), dependent upon the optical capabilities of the system, within which a suitable image may be captured. More particularly, the lasers are activated and deactivated (e.g. "on" and "off") in rapid succession such that, to the human eye it appears as though the lasers are "on", whereas the imaging systems are capable of detecting the sequential activation and deactivation. When the imaging systems take images in succession, the processor can take the laser location from image 1 (laser 24L) and compare that to image 2 (Laser 24R). The processor can then calculate the distance of the apparatus from the subject. It can also then calculate the size of the pixels in the AOI and SOI, thus allowing for very accurate measurement of the target (SOI).

In accordance with a further aspect of the present invention, the user is provided with feedback, either audible (e.g. beeps or tones) or visual LED indication (e.g. red, yellow, and green lights) that inform the user whether the imaging apparatus is within a suitable distance for an image capture. As imaging apparatus 10 is brought in proximity to the subject LEDs may flash from "red" (i.e. too far), to "yellow" (i.e. near range), to "green" (i.e. within range). As should be apparent the "red," "yellow," and "green," visual indications may be generated on the visual display 19.

Accordingly, light beam emitters 24 allow the user to repeatedly position the imaging apparatus at the same distance from the patient when capturing images. This feature ensures that images of the subject of interest (e.g. lesion) are taken from the same distance thereby allowing the medical professional to compare images taken at different times and determine changes in the appearance of lesions.

The captured images are temporarily stored in internal memory provided with the imaging apparatus. A dock is provided for holding the imaging apparatus when not in use, while further functioning to re-charge the battery power source. The imaging apparatus is adapted to download captured images to an electronic health records ("EHR") system, via hard-wire or wireless communication. Accordingly, images may be downloaded from the hand-held imaging device via USB connection, wireless local area network ("WIFI"), Ethernet standard (IEEE 802.3), open wireless technology (e.g. "Bluetooth"), or any other suitable communication means. The present invention thus provides a system and method for quickly and easily capturing consistent images of skin lesions or other areas/subjects of interest to provide medical professionals with an accurate and clear history.

Figure 7:
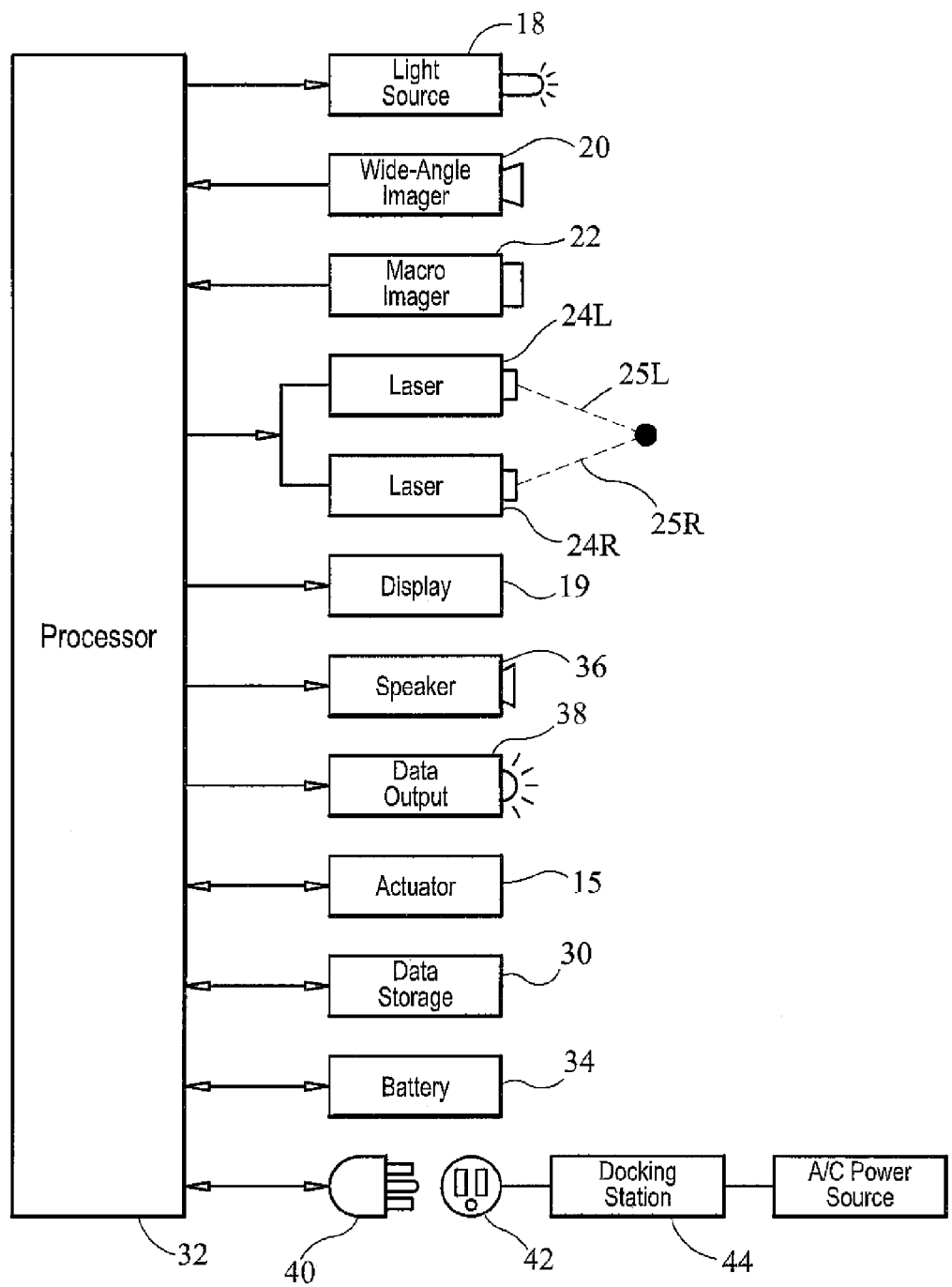
FIG. 7 is an electrical schematic block diagram illustrating an imaging apparatus in accordance with the present invention.

FIG. 7 is an electrical schematic block diagram for an imaging apparatus in accordance with the present invention. A battery power source 30 is contained within housing 12 to provide power for imaging apparatus 10. Battery power source 30 is preferably a rechargeable. A computer processor 32 is in electrical communication with battery power source 30 and functions to provide overall control of components. Light source 18, wide-angle imager 20, macro imager 22, and laser emitters 24, are all in electrical communication with processor 32. A data storage device 34 is electrically connected to processor 32 and functions to provide imaging apparatus 10 with internal memory. Data storage device 34 may comprise flash RAM, hard drive, removable hard drive, optical storage device, or any other suitable data storage device. Output devices, including electronic display 19, a speaker 36, and an optional wireless output transmitter 38 are also in electrical communication with processor 32. Electronic display 19 may comprise a liquid crystal display (LCD) or any other suitable display. Speaker 36 is in electronic communication with processor 32 and data storage device 34 and preferably functions to broadcast info nation, tones, and instructions to the user regarding operational aspects of imaging apparatus 10. The optional wireless output transmitter 38 may comprise an infrared transmitter, wireless RF transmitter, or any other suitable output device. Processor 32 is further in electrical communication with a docking connector 40 that functions to facilitate mating engagement with a mating connector 42 in electrical communication with a docking station 44. During normal operation, docking station 44 is electrically connected to an A/C power source 46 thereby, allowing docking station 44 to function both as a cradle and charging dock for imaging apparatus 10.

Figure 8A:
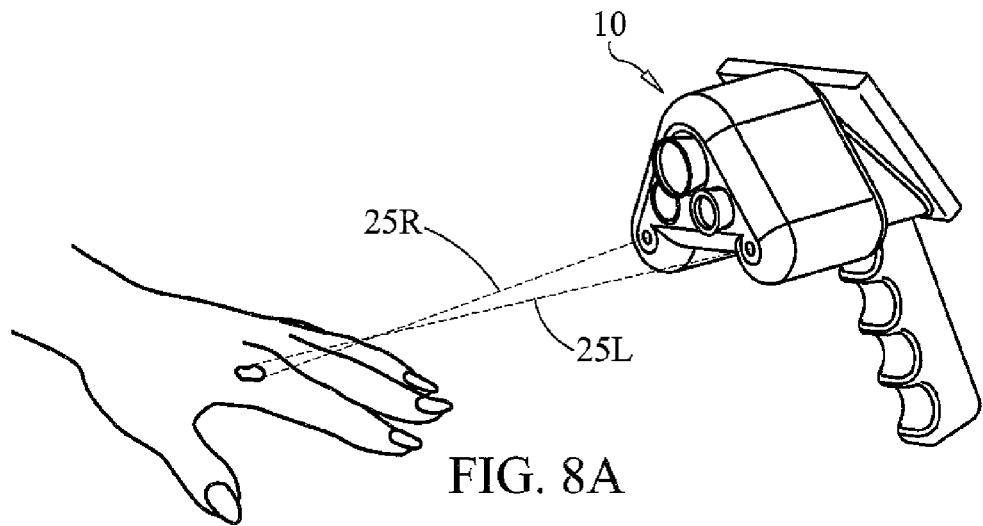
FIGS. 8A, 8B, and 8C illustrate use of the laser range finder apparatus and method associated with an imaging apparatus in accordance with the present invention.
Figure 8B:
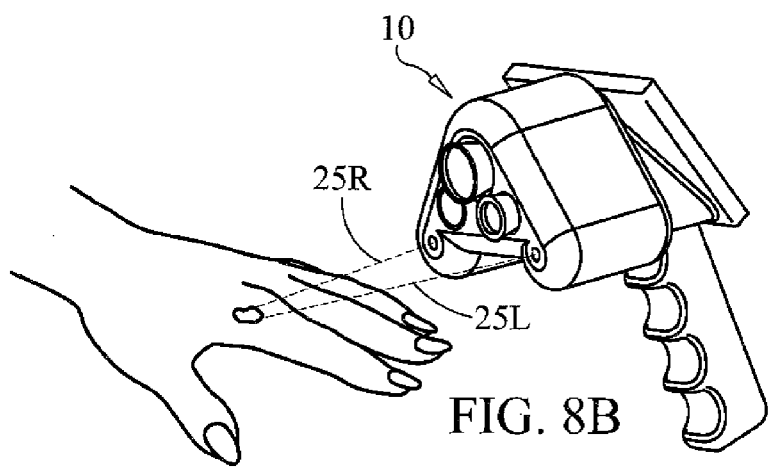
Figure 8C:
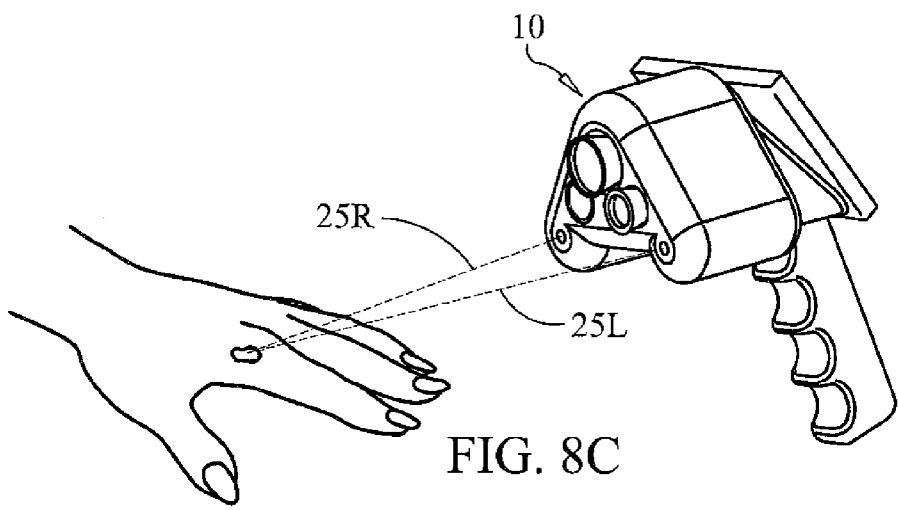

FIG. 8 illustrates use of the laser range finder apparatus and method associated with an imaging apparatus in accordance with the present invention in relation to the Subject of Interest ("SOI") on a patient. Although the laser range finding feature of the present invention is disclosed herein in connection with two spaced lasers (e.g. left and right hand configurations), referenced as 24L and 24R in FIG. 8, any suitable number of lasers (e.g. 3 or more) may be employed. As discussed above, imaging apparatus 10 includes a pair of laser beam projecting devices 24 that are installed in laterally spaced relation (e.g. left and right configurations) and angularly disposed such that the respective beams intersect at a predetermined distance from the front 16 of imaging device 10 so as to provide the user with a visual indication when the imaging device is the proper distance from the subject. FIG. 8A illustrates imaging apparatus 10 positioned too far from a patient's hand such that left and right beams, referenced as 25L and 25R, have crossed the point of intersection and begin to diverge from one another. The processor 32 is capable of determining that the target in FIG. 8A is on the far side of the laser angle convergence. FIG. 8B illustrates imaging apparatus 10 positioned too close to the patient's hand such that left and right beams 25L and 25R reflect on the patient's hand prior to intersection and/or convergence. The processor 32 is capable of determining that the target in FIG. 8B nearer than the target in FIG. 8B Finally, FIG. 8C illustrates imaging apparatus 10 properly positioned relative to the patient's hand such that beams 25L and 25R intersect at or near the subject of interest (SOI).

As should now be apparent, the imaging apparatus in accordance with the present invention, is capable of producing accurate digital images of suitable quality for identification and tracking of any Area of Interest ("AOI") of any Subject of Interest ("SOI"), including the identification and tracking of distinguishing lesions and/or characteristics on a person, pet, or object. The images may be downloaded via a docking station 44, or alternately may be wirelessly downloaded using output device 38.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A hand-held dermatological imaging apparatus adapted for simultaneously capturing images of a target subject of interest and a surrounding area of interest on a patient, said imaging apparatus comprising:

a main body including a front portion, a rear portion, and a handle, said handle including a manual actuator;

said main body including a battery power source, a computer processor electrically connected to said battery power source, and a data storage device configured to store digital data, and an electronic display disposed on the rear portion of the main body;

a light source configured to provide illumination from the front portion of said main body;

first and second digital imaging systems, each imaging system having a lens disposed on the front portion of said main body;

said first imaging system comprising a wide-angle system configured to capture an image of an area of interest on a patient;

said second imaging system comprising a macro system configured to capture an image of the target subject of interest which falls within the area of interest;

a pair of spaced light beam emitters configured to project beams of light from the front portion of said main body, said light beam emitters being angularly disposed so as to project converging beams of light from the front of said main body;

said pair of spaced light beam emitters modulated and configured for rapid alternating activation so as to project alternating first and second beams of light toward the patient and within said area of interest;

said first beam of light generating a first reflecting beam from a first point on the patient, and said second beam of light generating a second reflecting beam from a second point on the patient;

at least one of said first and second imaging systems configured to detect reflectance locations from the patient from each of said alternating fist and second beams of modulated light and said computer processor identifying pixel location for each of said reflectance locations, determining the spacing between said pixel locations and using said spacing to calculate in real time the distance of said main body from the patient based on the distance between said first and second reflectance locations;

means for providing output indicating when said main body is within a predetermined range for suitable image capture;

said manual actuator configured to generally simultaneously activate said first and second digital imaging systems such that images of the target subject of interest and the surrounding area of interest are captured;

said images being stored by said data storage device.

2. A hand-held dermatological imaging apparatus according to claim 1, wherein said means for providing output comprises a visual output indication on said electronic display.

3. A hand-held dermatological imaging apparatus according to claim 1, wherein said means for providing output comprises audible output.

4. A hand-held dermatological imaging apparatus according to claim 1, further including a docking station configured to cradle said main body when the imaging system is not in use, said docking station electrically connected to an A/C power source and configured to charge the battery power source when said main body is received on said docking station.

* * * * *